United States Patent
Hertz

(10) Patent No.: US 8,231,386 B2
(45) Date of Patent: Jul. 31, 2012

(54) TOOTH-IMPLANT METHOD AND APPLIANCE

(76) Inventor: Paul Hertz, Bronx, NY (US)

( * ) Notice: Subject to any disclaimer, the term of this patent is extended or adjusted under 35 U.S.C. 154(b) by 6 days.

(21) Appl. No.: 12/643,283

(22) Filed: Dec. 21, 2009

(65) Prior Publication Data

US 2010/0190137 A1 Jul. 29, 2010

Related U.S. Application Data

(60) Provisional application No. 61/203,264, filed on Dec. 19, 2008.

(51) Int. Cl.
*A61C 8/00* (2006.01)
(52) U.S. Cl. .......................... 433/173; 433/76
(58) Field of Classification Search .................. 433/75, 433/76, 219, 220, 173, 215; 606/96–98
See application file for complete search history.

(56) References Cited

U.S. PATENT DOCUMENTS

| 4,260,383 | A | * | 4/1981 | Weissman | 433/225 |
|---|---|---|---|---|---|
| 4,998,881 | A | * | 3/1991 | Lauks | 433/173 |
| 5,133,660 | A | * | 7/1992 | Fenick | 433/76 |
| 5,320,529 | A | * | 6/1994 | Pompa | 433/76 |
| 5,556,278 | A | | 9/1996 | Meitner | 433/75 |
| 5,636,986 | A | * | 6/1997 | Pezeshkian | 433/76 |
| 5,915,962 | A | * | 6/1999 | Rosenlicht | 433/76 |
| 5,967,777 | A | * | 10/1999 | Klein et al. | 433/75 |
| 6,364,664 | B1 | * | 4/2002 | Watanabe | 433/174 |
| 6,869,282 | B2 | * | 3/2005 | Carmichael et al. | 433/76 |
| 6,869,283 | B2 | | 3/2005 | Sussman | 433/76 |
| 6,986,661 | B2 | * | 1/2006 | Kim | 433/181 |
| 7,097,451 | B2 | * | 8/2006 | Tang | 433/76 |
| 7,104,795 | B2 | * | 9/2006 | Dadi | 433/72 |
| 7,153,132 | B2 | * | 12/2006 | Tedesco | 433/76 |
| 7,163,396 | B2 | * | 1/2007 | Gordils Wallis | 433/72 |
| 7,429,175 | B2 | | 9/2008 | Gittelson | |
| 7,574,025 | B2 | | 8/2009 | Feldman | 382/128 |
| 7,654,823 | B2 | * | 2/2010 | Dadi | 433/72 |
| 7,731,497 | B2 | * | 6/2010 | De Moyer | 433/72 |
| 7,845,943 | B2 | * | 12/2010 | Meitner | 433/75 |
| 7,905,726 | B2 | * | 3/2011 | Stumpel | 433/75 |
| 2002/0137003 | A1 | * | 9/2002 | Knapp | 433/76 |
| 2003/0165791 | A1 | * | 9/2003 | Carmichael et al. | 433/72 |
| 2004/0048225 | A1 | * | 3/2004 | Fletcher | 433/76 |
| 2004/0219480 | A1 | * | 11/2004 | Malin | 433/75 |
| 2007/0065777 | A1 | * | 3/2007 | Becker | 433/173 |
| 2007/0154862 | A1 | * | 7/2007 | Kim | 433/72 |
| 2009/0286201 | A1 | * | 11/2009 | Choe | 433/165 |
| 2010/0159412 | A1 | * | 6/2010 | Moss et al. | 433/24 |

* cited by examiner

*Primary Examiner* — Cris L Rodriguez
*Assistant Examiner* — Hao D Mai
(74) *Attorney, Agent, or Firm* — Andrew Wilford

(57) ABSTRACT

A tooth implant is done by first fitting to teeth adjacent an edentulous site of a jawbone a temporary bridge and providing in the bridge a guide tube oriented in alignment with a location on the site where an implant pin is to be seated. Then, with the bridge in place and using the tube as a guide, a pilot bore is drilled in the jawbone at the location, and then the implant pin is fitted into the drilled bore and the tube is plugged. The bridge with the plugged tube in place at the site during an osseointegration period after which the bridge is removed and replaced with a prosthesis anchored to the implant.

10 Claims, 2 Drawing Sheets

TOOTH-IMPLANT METHOD AND APPLIANCE

CROSS REFERENCE TO RELATED APPLICATION

This application is related to my provisional application 61/203,264 entitled "Hertz Appliance" and filed 19 Dec. 2008.

FIELD OF THE INVENTION

The present invention relates to tooth implants. More particularly this invention concerns a method if implanting one or more teeth and an appliance for use in the method.

BACKGROUND OF THE INVENTION

The basic procedures of replacing a missing tooth with an implant comprise the steps of sequentially:
1. Drilling a hole in the mandible at the edentulous site. This is typically done by first drilling a small-diameter pilot bore, then enlarging it with a bit dimensioned identically to the pin to be set.
2. Setting a titanium pin comprising the first stage of the actual implant in the hole. The pin typically is formed with an outwardly open threaded bore that is closed by a removable screw.
3. If the implant site is visible it may be necessary for cosmetic purposes to fit the patient at this time with a temporary bridge. This is also necessary when the implant is replacing an existing tooth or bridge to prevent the adjacent teeth from shifting.
4. Leaving the set pin in the jaw for an osseointegration period that may be weeks or months long. During this time the mandible fuses to the sides of the pin, and normally the gum tissue grows back over the outer end of the pin.
5. After removing any tissue covering the outer end of the osseointegrated pin, replacing the screw with a second stage, typically a ball that projects up past the ablated gum tissue.
6. Subsequently, in some cases after a certain time to permit the gum tissue to heal and stabilize, taking an impression and making a crown or prosthesis to fit at the edentulous site over the second stage.

The exact position of the pin is extremely critical. It must be solidly anchored in the mandible and must also be centered in the edentulous site. In many cases the drilling and setting of the pin and even of the second stage is carried out by an oral surgeon, not by the dentist who does the other steps of the procedure. Thus there is frequently the problem that the surgeon sets an implant in a location making it difficult for the dentist to properly construct and anchor the crown.

Numerous procedures are known for determining alignment of the pilot bore. For example U.S. Pat. Nos. 5,636,986, 6,869,283, and 7,097,451 describe guides, templates, and jigs used to guide the drill. Such devices are complex, must be set up by the oral surgeon, and are designed to be fitted to the patient and only used after their orientation has been confirmed, typically by an x-ray. The dentist who must later set the implant, has little control over the use of this tool, so that the problem remains that the surgeon may set the implant in a location that is not what the dentist wants.

OBJECTS OF THE INVENTION

It is therefore an object of the present invention to provide an improved tooth-implant method.

Another object is the provision of such an improved tooth-implant method that overcomes the above-given disadvantages, in particular that ensures that the first bore in the mandible is ideally positioned.

A further object is to provide an improved dental appliance that facilitates and simplifies the method according to the invention.

SUMMARY OF THE INVENTION

A tooth implant is done according to the invention by first fitting to teeth adjacent an edentulous site of a jawbone a temporary bridge and providing in the bridge a guide tube oriented in alignment with a location on the site where an implant pin is to be seated. Then, with the bridge in place and using the tube as a guide, a pilot bore is drilled in the jawbone at the location, and then the implant pin if fitted into the drilled bore and the tube is plugged. The bridge with the plugged tube in place at the site during an osseointegration period after which the bridge is removed and replaced with a prosthesis anchored to the implant.

Thus with this procedure the dentist who prepares the site, for instance by extracting a bad tooth, is responsible for determining the exact orientation of the actual implant. This is done by radiography or other standard dental procedures. The bridge therefore not only serves a cosmetic and spacer function, but also acts as the drilling jig or guide.

According to a further feature of the invention, after osseointegration which normally entails gum tissue growing over the outer end of the implant, the guide tube can be unplugged and the tube can be used again to drill or cut through the gum. Once the outer end of the implant is exposed, the screw closing its threaded bore is extracted and replaced with a the second-stage of the implant, the ball or abutment to which the eventual crown is anchored. Since the guide tube was used to position the implant, it will be perfectly aligned with overgrown implant so the dentist can uncover the implant simply, without any need to take additional x-rays or make any exploratory incisions. Hence the tube-equipped bridge of this invention is used twice during the implant procedure, substantially simplifying it.

Furthermore, once the second stage is mounted on the implant the bridge appliance according to the invention can be hollowed out to fit over it and function both cosmetically and as a spacer. It also protects the site during healing of the gingival tissue around the implant, and during the time it takes to make the final crown that will be installed. Thus at a third time in the tooth-implant procedure this bridge fulfills a useful function. What is more, the fact that the bridge is provided to the patient from the very start of the procedure to the very end, means that the entire procedure can be allowed to take place over a time frame that is ideal for healing and fits with both the patient's and dentist's schedule, as opposed to the normally rushed schedule most patients want.

In the system of this invention the dentist images the edentulous site, typically with an x-ray, and also takes an impression as the first step. The impression is used in the standard manner to form the bridge while the x-ray serves for orientation of the guide tube in the bridge. Semielastic clips are provided on the bridge that hold it securely in place, but that allow it to be removed, even by the patient, when necessary. Normally the entire bridge is made of molded plastic, but the guide tube is metallic and dimensioned to correspond to a standard pilot bit. The clips are transparent while the body of the bridge is of course modeled and colored to match the adjacent teeth.

BRIEF DESCRIPTION OF THE DRAWING

The above and other objects, features, and advantages will become more readily apparent from the following description, reference being made to the accompanying drawing in which.

SPECIFIC DESCRIPTION

Figure 2:
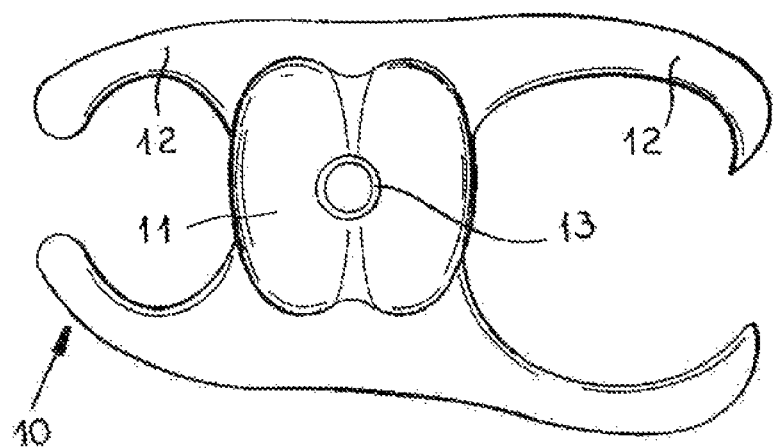
FIG. 2 is a top view of the appliance according to the invention.

With reference to FIG. 2, an appliance 10 for carrying out the instant invention comprises basically a colored-plastic center body or crown 11 and a pair of clear plastic clips 12. The crown 11 is provided with a metallic tube 13.

Figure 1:
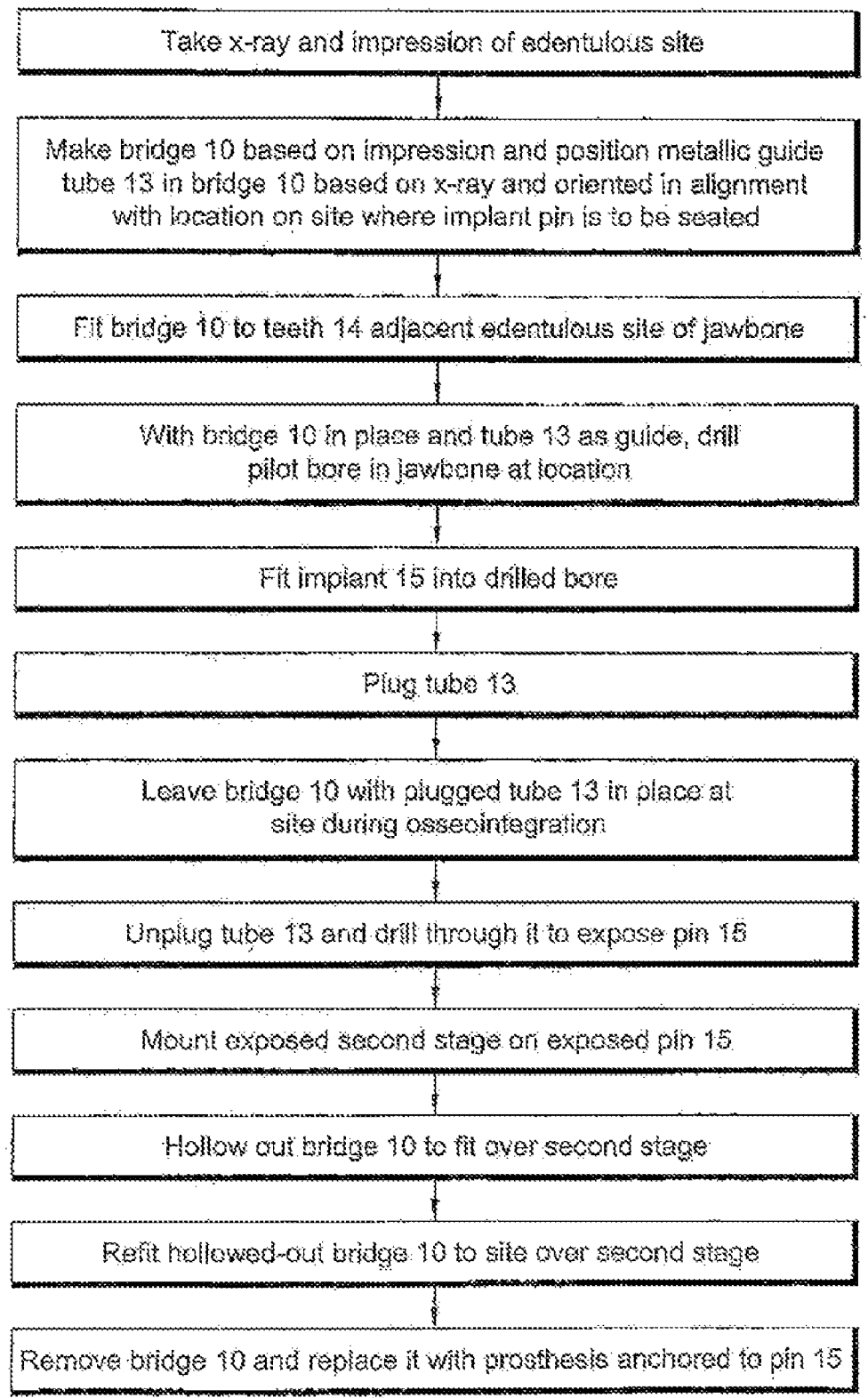
FIG. 1 is a block diagram describing the method of this invention.
Figure 3:
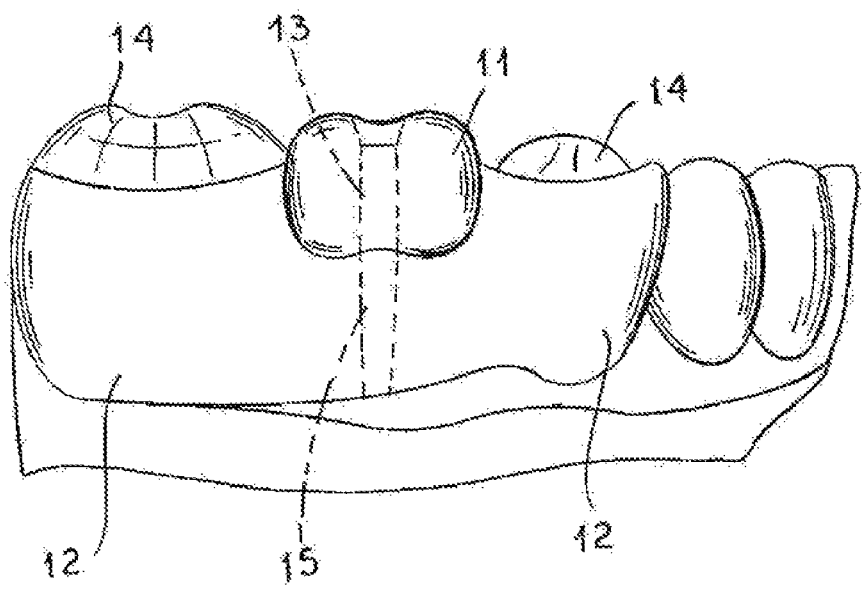
FIGS. 3 and 4 are side and top views of the appliance when installed.
Figure 4:
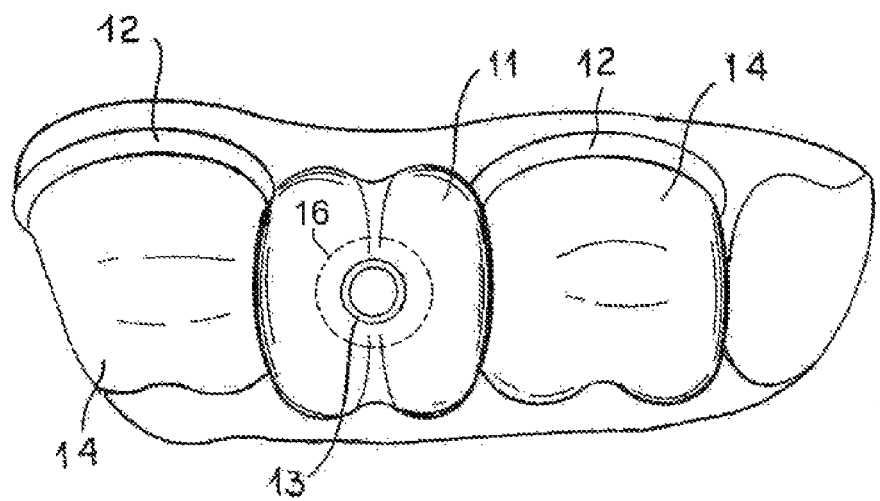

This appliance is used as seen in FIGS. 1, 3, and 4 in a method comprising the steps of sequentially:

1. Taking an x-ray and an impression of an edentulous site;
2. Making the bridge 10 based on the impression and positioning the metallic guide tube 13 in the bridge 10 based on the x-ray and oriented in alignment with a location on the site where an implant pin is to be seated;
3. Fitting the bridge 10 to teeth 14 adjacent the edentulous site of a jawbone;
4. With the bridge 10 in place and using the tube 13 as a guide, drilling a pilot bore in the jawbone at the location;
5. Fitting an implant body or pin 15 into the drilled bore, normally after removing the bridge and enlarging the pilot bore;
6. Plugging the tube 13;
7. Leaving the bridge 10 with the plugged tube 13 in place at the site during an osseointegration period;
8. Unplugging the tube 13 and working through it to expose the pin 15 by drilling through the tube 13 into any gum tissue overlying the implant;
9. Mounting an exposed second stage 16 on the exposed pin 15;
10. Hollowing out the bridge 10 to fit over the second stage;
11. Refitting the hollowed-out bridge 10 to the site over the second stage; and
12. Removing the bridge 10 and replacing it with a prosthesis anchored to the implant.

I claim:

1. A tooth-implant method comprising the steps of sequentially:
   a) fitting to teeth adjacent an edentulous site of a jawbone a temporary bridge and providing in the bridge a guide tube oriented in alignment with a location on the site where an implant pin is to be seated;
   b) with the bridge in place and using the tube as a guide, drilling a pilot bore in the jawbone at the location;
   c) fitting the implant pin into the drilled bore;
   d) plugging the tube;
   e) leaving the bridge with the plugged tube in place at the site during an osseointegration period; and
   f) after the osseointegration period removing the bridge and replacing it with a prosthesis anchored to the implant pin.

2. The tooth-implant method defined in claim 1, further comprising the steps after step e) and before step f) of:
   e') unplugging the tube and exposing the implant pin with the bridge in place at the site; and
   e") mounting an exposed second stage on the exposed implant pin, the prosthesis being subsequently anchored to the second stage.

3. The tooth-implant method defined in claim 2 wherein in step e') the implant pin is exposed by drilling through the tube into any gum tissue overlying the implant pin.

4. The tooth-implant method defined in claim 1, further comprising the steps after step e) and before step f) of:
   e') mounting on the implant pin a second stage;
   e") hollowing out the bridge to fit over the second stage; and
   e"') refitting the hollowed-out bridge to the site over the second stage.

5. The tooth-implant method defined in claim 1 wherein step a) includes the steps of:
   $a_1$) taking an x-ray and an impression of the edentulous site;
   $a_2$) making the bridge based on the impression and positioning the guide tube in the bridge based on the x-ray.

6. The tooth-implant method defined in claim 5 wherein step a) further includes the step of:
   $a_3$) providing on the bridge clips engageable around bases of the adjacent teeth.

7. The tooth-implant method defined in claim 6 wherein the clips are made of semielastic plastic.

8. The tooth-implant method defined in claim 7 wherein the clips are at least semitransparent.

9. The tooth-implant method defined in claim 6 wherein the bridge is made of a molded nonmetallic material and the guide tube is metallic.

10. The tooth-implant method defined in claim 1, further comprising the steps between steps b) and c) of:
    b') removing the bridge;
    b") enlarging the pilot bore with a bit of larger diameter than that used to form the pilot bore, the method further comprising the step between steps d) and e) of:
    d') refitting the bridge to the site.

* * * * *